United States Patent [19]

Evans et al.

[11] Patent Number: 5,432,055
[45] Date of Patent: Jul. 11, 1995

[54] **DETECTION OF *PORPHYROMONAS GINGIVALIS***

[76] Inventors: Mary J. Evans; Richard T. Evans, both of 38 Fiddler's Green, East Amherst, N.Y. 14051; Robert J. Genco, 32 St. Catherines Ct., Buffalo, N.Y. 14222; Steven J. Greenberg, 42 Hillsboro Dr., Orchard Park, N.Y. 14127; Howard K. Kuramitsu, 6091 Meadowlakes Dr., Clarence, N.Y. 14031

[21] Appl. No.: 72,067

[22] Filed: Jun. 2, 1993

[51] Int. Cl.$^6$ .................... C12Q 1/68; C12P 19/34; C07H 21/04
[52] U.S. Cl. ........................ 435/6; 435/91.2; 536/24.32; 536/24.33; 935/77; 935/78
[58] Field of Search .............. 435/6, 91.2; 536/24.32, 536/24.33, 23.7; 514/44; 935/77, 78

[56] References Cited

U.S. PATENT DOCUMENTS 4,977,251 12/1990 Salyers et al. .......................... 536/27
4,994,376  2/1991 Zambon et al. ....................... 435/24

OTHER PUBLICATIONS

Kato et al. J. Bacteriol (1992) 174:3889–3895.
Dickinson J. Bacteriol (1988) 170:1658–1665.
Choi et al. Infect Immun. (1991) 59:1564–1566.
Kuritza et al., "Enumeration of Polysaccharide-Degrading Bacteroides Species in Human Feces by Using Species-Specific DNA Probes", Applied and Environmental Microbiology, vol. 51, No. 2, Feb. 1986 pp. 385–390.

*Primary Examiner*—Margaret Parr
*Assistant Examiner*—Carla Myers
*Attorney, Agent, or Firm*—Hodgson, Russ, Andrews, Woods & Goodyear

[57] ABSTRACT

The present invention relates to novel compositions comprising *P. gingivalis* specific oligonucleotides which are useful as primers to amplify particular regions of the genome of *P. gingivalis* during enzymatic nucleic acid amplification. The invention also provides a method for the detection of *P. gingivalis*, which may be present in a clinical specimen, using the *P. gingivalis*-specific primers and enzymatic nucleic acid amplification. The present invention also relates to *P. gingivalis*-specific oligonucleotides which are useful as probes to facilitate detection of the amplified regions of *P. gingivalis* DNA.

13 Claims, 6 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 21 nucleotides
        ( B ) TYPE: nucleic acid
        ( C ) STRANDEDNESS: single-stranded
        ( D ) TOPOLOGY: linear (ii) ORIGINAL SOURCE:
        (A) ORGANISM: Porphyromonas gingivalis
        (B) STRAIN: 381

(iii) FEATURE:
        (A) LOCATION: Genbank Locus BNGFIMA, 269-289
        (B) IDENTIFICATION METHOD: by experiment
        (C) OTHER INFORMATION: hybridizes to Porphyromonas
              gingivalis fimbrial gene region (iv) PUBLICATION INFORMATION:
        (A) AUTHORS: Dickinson, Douglas P.; Kubiniec, Michael A.;
              Yoshimura, Fuminobou; and Genco, Robert J.
        (B) TITLE: Molecular Cloning and Sequencing of the Gene
              Encoding the Fimbrial Subunit Protein of Bacteroides
              gingivalis
        (C) JOURNAL: Journal of Bacteriology
        (D) VOLUME: 170
        (E) ISSUE: 4
        (F) PAGES: 1658-1665
        (G) DATE: April 1988

(v) SEQUENCE DESCRIPTION: SEQ ID NO:1:

TTTGGAGTTG GCGATGACGA A            21

(2) INFORMATION FOR SEQ ID NO:2:

(i) SEQUENCE CHARACTERISTICS:
        (A) LENGTH: 21 nucleotides
        (B) TYPE: nucleic acid
        (C) STRANDEDNESS: single-stranded
        (D) TOPOLOGY: linear (ii) ORIGINAL SOURCE:
        (A) ORGANISM: Porphyromonas gingivalis
        (B) STRAIN: 381

(iii) FEATURE:
        (A) LOCATION: Genbank Locus BNGFIMA, 452-472
        (B) IDENTIFICATION METHOD: by experiment
        (C) OTHER INFORMATION: hybridizes to Porphyromonas
              gingivalis fimbrial gene region (iv) PUBLICATION INFORMATION:
        (A) AUTHORS: Dickinson, Douglas P.; Kubiniec, Michael A.;
              Yoshimura, Fuminobou; and Genco, Robert J.
        (B) TITLE: Molecular Cloning and Sequencing of the Gene
              Encoding the Fimbrial Subunit Protein of Bacteroides
              gingivalis
        (C) JOURNAL: Journal of Bacteriology
        (D) VOLUME: 170
        (E) ISSUE: 4
        (F) PAGES: 1658-1665
        (G) DATE: April 1988

(v) SEQUENCE DESCRIPTION: SEQ ID NO:2:

GCTTTTACCT CTGCAAGAGT C            21

(2) INFORMATION FOR SEQ ID NO:3:

(i) SEQUENCE CHARACTERISTICS:
        (A) LENGTH: 41 nucleotides
        (B) TYPE: nucleic acid
        (C) STRANDEDNESS: single-stranded
        (D) TOPOLOGY: linear (ii) ORIGINAL SOURCE:
        (A) ORGANISM: Porphyromonas gingivalis
        (B) STRAIN: 381

(iii) FEATURE:
        (A) LOCATION: Genbank Locus BNGFIMA, 299-338
        (B) IDENTIFICATION METHOD: by experiment
        (C) OTHER INFORMATION: hybridizes to Porphyromonas
              gingivalis fimbrial gene region (iv) PUBLICATION INFORMATION:

(A) AUTHORS: Dickinson, Douglas P.; Kubiniec, Michael A.;
    Yoshimura, Fuminobou; and Genco, Robert J.
(B) TITLE: Molecular Cloning and Sequencing of the Gene
    Encoding the Fimbrial Subunit Protein of Bacteroides
    gingivalis
(C) JOURNAL: Journal of Bacteriology
(D) VOLUME: 170
(E) ISSUE: 4
(F) PAGES: 1658-1665
(G) DATE: April 1988

(v) SEQUENCE DESCRIPTION: SEQ ID NO:3:

AAGGTGGCTA AGTTGACCGT AATGGTTTAT AATGGAGAAC A        41

(2) INFORMATION FOR SEQ ID NO:4:

(i) SEQUENCE CHARACTERISTICS:
        (A) LENGTH: 40 nucleotides
        (B) TYPE: nucleic acid
        (C) STRANDEDNESS: single-stranded
        (D) TOPOLOGY: linear (ii) ORIGINAL SOURCE:
        (A) ORGANISM: Porphyromonas gingivalis
        (B) STRAIN: ATCC 53977

(iii) FEATURE:
        (A) LOCATION: Genbank Locus BNGSOD, 115-154
        (B) IDENTIFICATION METHOD: by experiment
        (C) OTHER INFORMATION: hybridizes to Porphyromonas
            gingivalis superoxide dismutase gene region (iv) PUBLICATION INFORMATION:
        (A) AUTHORS: Choi, Jeom-Il; Takahashi, Nobuyoshi; Kato,
            Tetsuo; Kuramitsu, Howard K.
        (B) TITLE: Isolation, Expression, and Nucleotide Sequence
            of the sod Gene from Porphyromonas gingivalis
        (C) JOURNAL: Infection and Immunity
        (D) VOLUME: 59
        (E) ISSUE: 4
        (F) PAGES: 1564-1566
        (G) DATE: April 1991

(v) SEQUENCE DESCRIPTION: SEQ ID NO:4:

ATTTCCCTGC CTTATGCGGT CGATGCACTG GCTCCTGTTA        40

(2) INFORMATION FOR SEQ ID NO:5:

(i) SEQUENCE CHARACTERISTICS:
        (A) LENGTH: 39 nucleotides
        (B) TYPE: nucleic acid
        (C) STRANDEDNESS: single-stranded
        (D) TOPOLOGY: linear (ii) ORIGINAL SOURCE:
        (A) ORGANISM: Porphyromonas gingivalis
        (B) STRAIN: ATCC 53977

(iii) FEATURE:
        (A) LOCATION: Genbank Locus BNGSOD, 571-606
        (B) IDENTIFICATION METHOD: by experiment
        (C) OTHER INFORMATION: hybridizes to Porphyromonas
            gingivalis superoxide dismutase gene region (iv) PUBLICATION INFORMATION:
        (A) AUTHORS: Choi, Jeom-Il; Takahashi, Nobuyoshi; Kato,
            Tetsuo; Kuramitsu, Howard K.
        (B) TITLE: Isolation, Expression, and Nucleotide Sequence
            of the sod Gene from Porphyromonas gingivalis
        (C) JOURNAL: Infection and Immunity
        (D) VOLUME: 59
        (E) ISSUE: 4
        (F) PAGES: 1564-1566
        (G) DATE: April 1991

(v) SEQUENCE DESCRIPTION: SEQ ID NO:5:

ACGATTCTGG TAAGTCAGAT AATATGCGTG CTCCCATGC        39

( 2 ) INFORMATION FOR SEQ ID NO:6:

( i ) SEQUENCE CHARACTERISTICS:
        ( A ) LENGTH: 40 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Porphyromonas gingivalis
        ( B ) STRAIN: ATCC 53977

( i i i ) FEATURE:
        ( A ) LOCATION: Genbank Locus BNGSOD, 406-445
        ( B ) IDENTIFICATION METHOD: by experiment
        ( C ) OTHER INFORMATION: hybridizes to Porphyromonas
            gingivalis superoxide dismutase gene region ( i v ) PUBLICATION INFORMATION:
        ( A ) AUTHORS: Choi, Jeom-Il; Takahashi, Nobuyoshi; Kato,
            Tetsuo; Kuramitsu, Howard K.
        ( B ) TITLE: Isolation, Expression, and Nucleotide Sequence
            of the sod Gene from Porphyromonas gingivalis
        ( C ) JOURNAL: Infection and Immunity
        ( D ) VOLUME: 59
        ( E ) ISSUE: 4
        ( F ) PAGES: 1564-1566
        ( G ) DATE: April 1991

( v ) SEQUENCE DESCRIPTION: SEQ ID NO:6:

```
TCATTCGAAA AGTTCAAAGA GGAGTTCAAC ACAGCCGGTA          40
```

( 2 ) INFORMATION FOR SEQ ID NO:7:

( i ) SEQUENCE CHARACTERISTICS:
        ( A ) LENGTH: 41 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Porphyromonas gingivalis
        ( B ) STRAIN: ATCC 53977

( i i i ) FEATURE:
        ( A ) LOCATION: Genbank Locus GNGCLGNS, 197-237
        ( B ) IDENTIFICATION METHOD: by experiment
        ( C ) OTHER INFORMATION: hybridizes to Porphyromonas
            gingivalis collagenase gene region ( i v ) PUBLICATION INFORMATION:
        ( A ) AUTHORS: Kato, Tetsuo; Takahashi, Nobuyoshi; Kuramitsu,
            Howard K.
        ( B ) TITLE: Sequence Analysis and Characterization of the
            Porphyromonas gingivalis prtC Gene, Which Expresses a
            Novel Collagenase Activity
        ( C ) JOURNAL: Journal of Bacteriology
        ( D ) VOLUME: 174
        ( E ) ISSUE: 12
        ( F ) PAGES: 3889-3895
        ( G ) DATE: June 1992

( v ) SEQUENCE DESCRIPTION: SEQ ID NO:7:

```
ATCTGTCCAC TCAGCTCAAT ATCAGCAATG CGGAAGCCCT A          41
```

( 2 ) INFORMATION FOR SEQ ID NO:8:

( i ) SEQUENCE CHARACTERISTICS:
        ( A ) LENGTH: 33 nucleotides
        ( B ) TYPE: nucleic acid
        ( C ) STRANDEDNESS: single- stranded
        ( D ) TOPOLOGY: linear ( i i ) ORIGINAL SOURCE:
        ( A ) ORGANISM: Porphyromonas gingivalis
        ( B ) STRAIN: ATCC 53977

(iii) FEATURE:
  (A) LOCATION: Genbank Locus GNGCLGNS, 547-578
  (B) IDENTIFICATION METHOD: by experiment
  (C) OTHER INFORMATION: hybridizes to Porphyromonas
      gingivalis collagenase gene region (iv) PUBLICATION INFORMATION:
  (A) AUTHORS: Kato, Tetsuo; Takahashi, Nobuyoshi; Kuramitsu,
      Howard K.
  (B) TITLE: Sequence Analysis and Characterization of the
      Porphyromonas gingivalis prtC Gene, Which Expresses a
      Novel Collagenase Activity
  (C) JOURNAL: Journal of Bacteriology
  (D) VOLUME: 174
  (E) ISSUE: 12
  (F) PAGES: 3889-3895
  (G) DATE: June 1992

(v) SEQUENCE DESCRIPTION: SEQ ID NO:8:

ATCCATCATC TTATTGATGA AATGAATAGT CTT    33

(2) INFORMATION FOR SEQ ID NO:9:

(i) SEQUENCE CHARACTERISTICS:
    (A) LENGTH: 29 nucleotides
    (B) TYPE: nucleic acid
    (C) STRANDEDNESS: single-stranded
    (D) TOPOLOGY: linear (ii) ORIGINAL SOURCE:
    (A) ORGANISM: Porphyromonas gingivalis
    (B) STRAIN: ATCC 53977

(iii) FEATURE:
    (A) LOCATION: Genbank Locus GNGCLGNS, 403-431
    (B) IDENTIFICATION METHOD: by experiment
    (C) OTHER INFORMATION: hybridizes to Porphyromonas
        gingivalis collagenase gene region (iv) PUBLICATION INFORMATION:
    (A) AUTHORS: Kato, Tetsuo; Takahashi, Nobuyoshi; Kuramitsu,
        Howard K.
    (B) TITLE: Sequence Analysis and Characterization of the
        Porphyromonas gingivalis prtC Gene, Which Expresses a
        Novel Collagenase Activity
    (C) JOURNAL: Journal of Bacteriology
    (D) VOLUME: 174
    (E) ISSUE: 12
    (F) PAGES: 3889-3895
    (G) DATE: June 1992

(v) SEQUENCE DESCRIPTION: SEQ ID NO:9:

AAGTGCTATC TAAGCCTGCA CGAACACAA    29

DETECTION OF *PORPHYROMONAS GINGIVALIS*

This invention was made in part with government support under grants DE04898, DE08293 and DE00158 awarded by the National Institute of Dental Research. The government has certain rights in the invention.

FIELD OF THE INVENTION

The present invention relates to novel compositions and methods for detecting the presence of *Porphyromonas gingivalis*, bacteria associated with the development of periodontal disease. More particularly, the invention is directed to an accurate and sensitive method for the diagnosis of *P. gingivalis* infection using *P. gingivalis* specific oligonucleotides as primers to amplify particular regions of the genome of *P. gingivalis* which may be present in a clinical specimen. *P. gingivalis* specific oligonucleotides may be used in the subsequent detection of the amplified regions of DNA.

BACKGROUND OF THE INVENTION

*P. gingivalis* is a black-pigmented anaerobe that is associated with periodontal destruction in humans (Slots, 1977, *Scand. J. Dent. Res.* 85:247–354; Slots, 1986, *J. Clin. Periodontal.* 13:912–917; Socransky et al., 1990, p. 79–90 in J. D. Bader (ed.), *Risk assessment in dentistry*, University of North Carolina Dental Ecology, Chapel Hill). *P. gingivalis* is associated with several periodontal diseases including adult periodontitis, generalized juvenile periodontitis, periodontal abscesses, and refractory periodontitis. The tissues affected by periodontitis may include the gingival tissue, periodontal membrane, cementum, and the alveolar bone.

The organism is frequently found in low numbers when normal plaque is examined, or after treatment to reduce bacterial infection. Since it is unclear whether these low numbers represent a pathogenic threat, it is important to be able to quantitate, with accuracy and sensitivity, *P. gingivalis* in a given oral site in order to evaluate periodontal destruction potential. Current methods of detection of these fastidious organisms is dependent on culturing the bacteria or identifying the bacteria by immunofluorescence microscopy. *P. gingivalis* is difficult to cultivate on initial isolation due to its strict nutritional requirements and oxygen sensitivity (Zambon et all, 1988, *J. Periodontol.* 59:23–31). An example of current culture protocols involves inoculation onto enriched tryptic soy agar (ETSA) supplemented with 40 μg/ml kanamycin, and incubation for seven days at 37° C. in an anaerobic chamber containing 85% $N_2$, 10% $H_2$, and 5% $CO_2$. Resultant isolates can then be identifed according to established procedures including gram-stain characteristics, cellular and colonial morphology, requirement for anaerobiosis, fermentation of specific sugars, and biochemical tests. Thus, the time required for growth and to complete identification can range from 7 to 21 days. Detection of *P. gingivalis* can also be accomplished by using immunofluorescence microscopy (Zambon et al., 1985, *J. Periodontol.* (Suppl.) 56:32–40). Although indirect immunofluorescence microscopy of *P. gingivalis* appears highly sensitive and specific for this organism, false positive reactions likely are due to the difficulties inherent in culturing this strictly anaerobic microorganism. These techniques, culturing the organism or detecting the organism by immunofluorescence, are both labor and time intensive.

Recent advances in molecular biology have provided several means for enzymatically amplifying nucleic acid sequences. Currently the most commonly used method, PCR (polymerase chain reaction, Cetus Corporation) involves the use of Taq Polymerase, known sequences as primers, and heating cycles which separate the replicating deoxyribonucleic acid (DNA) strands and exponentially amplify a gene of interest. Other amplification methods currently under development include LCR (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA (nucleic acid sequence-based amplification, Cangene Corporation) which can be performed on RNA or DNA as the nucleic acid sequence to be amplified.

Nucleic acid probes that are capable of hybridization with specific gene sequences have been used successfuly to detect specific pathogens in biological specimens at levels of sensitivity approaching $10^3$–$10^4$ organisms per specimen. Whole chromosome probes, developed from genomic DNA isolated from *P. gingivalis* and *P. intermedius* strains, have been used successfully in identifying *P. gingivalis* and *P. intermedius* in 74–77% of adult periodontitis samples compared to 21–26% identification by cultural analysis (Groves, 1990, pp. 236–237, in *Gene Probe for Bacteria*, eds. Macario and deMacario, Academic Press) However, the use of whole chromosome probes requires $10^3$ *P. gingivalis* cells for positive detection, and may require isolation of the strains from the clinical sample before use of the whole chromosome probes because of overlapping sequence homology and differences in the quantitative makeup of the oral flora by Porphyromonas species.

Cloned random gene fragments from closely related Bacteroides species have been used to detect and enumerate *B. vulgaris* in human feces (Kuritza et al., 1986, *Appl. Environ. Microbiol.* 51:385–390). Also, random fragments of chromosomal DNA from several Bacteroides species were cloned into plasmids from which RNA probes were developed (Groves et al., 1987, *Diag. Microbiol. Infect. Dis.* 7:273–278). The resultant RNA probes were used to detect isolated strains of Bacteroides species at a sensitivity of about $10^6$ cells. However, in systems using cloned random fragments, the specificity may be reduced because of shared sequences among Bacteroides species, as compared to amplification and hybridization of species-specific gene sequences.

Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. The present invention is directed to primers which amplify species-specific sequences of known genes of *P. gingivalis*, and to probes which specifically hybridize with these amplified DNA fragments. By using the nucleic acid sequences of the present invention and according to the methods of the present invention, as few as one *P. gingivalis* organism may be detected in the presence of 10 µg/ml extraneous DNA.

SUMMARY AND OBJECTS OF THE INVENTION

The present invention is directed to nucleic acid sequences (oligonucleotides) useful as primers and/or probes in the detection of P. gingivalis in clinical specimens. Also, the present invention is directed to a method of detecting the presence of P. gingivalis in a clinical specimen wherein the oligonucleotides of the present invention may be used to amplify target nucleic acid sequences of P. gingivalis that may be contained within a clinical specimen, and/or to detect the presence or absence of amplified target nucleic acid sequences of P. gingivalis. The oligonucleotides may be used to amplify and/or detect P. gingivalis gene sequences corresponding to the fimbrial protein, superoxide dismutase, and collagenase.

One object of the present invention is to provide oligonucleotides which can be used as primers to amplify specific gene sequences of P. gingivalis.

Another object of the present invention is to provide oligonucleotides which can be used as probes in the detection of amplified specific gene sequences of P. gingivalis.

A further object of the present invention is to provide an accurate and sensitive method for detecting the presence of P. gingivalis that may be contained in clinical specimens by using the oligonucleotides disclosed to amplify and detect specific gene sequences of P. gingivalis.

BRIEF DESCRIPTION OF THE FIGURES

In the accompanying drawings.

DETAILED DESCRIPTION OF TEE INVENTION

Figure 1:
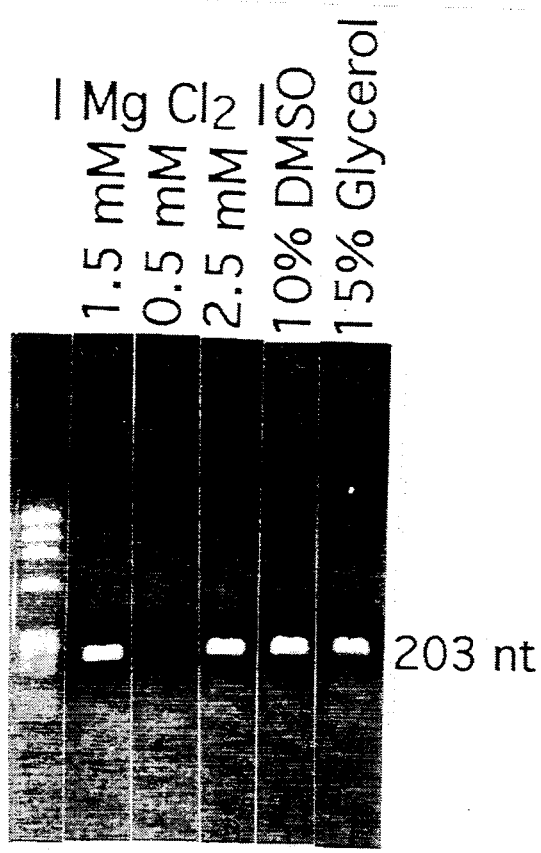
FIG. 1 represents an agarose gel corresponding to the amplification of P. gingivalis DNA, using the fimbrial gene primers of the present invention, in the presence of MgCl₂ at 1.5 mM, 0.5 mM, and 2.5 mM, or in 10% dimethylsulfoxide (DMSO) or 15% glycerol.

The present invention is directed to species-specific oligonucleotides which can be used to amplify sequences of P. gingivalis DNA, and to subsequently determine if amplification has occurred, from DNA extracted from a clinical specimen comprising saliva, tooth scrapings, subgingival material (paper points) or gingival tissue. In one embodiment of the present invention, a pair of P. gingivalis-specific DNA oligonucleotide primers are used to hybridize to P. gingivalis genomic DNA that may be present in DNA extracted from a clinical specimen, and to amplify the specific segment of genomic DNA between the two flanking primers using enzymatic synthesis and temperature cycling. Each pair of primers are designed to hybridize only to the P. gingivalis DNA to which they have been synthesized to complement; one to each strand of the double-stranded DNA. Thus, the reaction is specific even in the presence of microgram quantities of heterologous DNA. For the purposes of this description, the primer derived from the sequence of the positive strand of DNA will be referred to as the "positive primer", and the primer derived from the sequence of the negative strand will be referred to as the "negative primer".

Amplification of DNA may be accomplished by any one of the methods commercially available. For example, the polymerase chain reaction may be used to amplify the DNA. Once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled, and specific amplification of the P. gingivalis DNA sequences, if present, results. Further identification of the amplified DNA fragment, as being derived from P. gingivalis DNA, may be accomplished by liquid hybridization. This test utilizes one or more labeled oligonucleotides as probes to specifically hybridize to the amplified segment of P. gingivalis DNA. Detection of the presence of sequence-specific amplified DNA may be accomplished using any one of several methods known in the art such as a gel retardation assay with autoradiography. Thus, the oligonucleotides of the present invention have commercial applications in diagnostic kits for the detection of microorganisms associated with periodontal disease.

In another embodiment of the present invention, the species-specific oligonucleotides may be used to amplify and detect P. gingivalis DNA from DNA extracted from a clinical specimen. In this embodiment, the oligonucleotides used as primers may be labeled directly, or synthesized to incorporate label. Depending on the label used, the amplification products can then be detected, after binding onto an affinity matrix, using isotopic or colorimetric detection.

EXAMPLE I

DNA Extraction:

*P. gingivalis* was cultured for 48 hours in reduced Brain Heart Infusion (BHI) containing added 10% yeast extract, 10% trypticase, 10% peptone, 0.05% hemin, and 0.02% menadione. The bacteria were harvested and then washed and resuspended in TE buffer (10 mM Tris-HCl pH 8.0, 1 mM EDTA). DNA was extracted using a CTAB/NaCl miniprep protocol for isolation of bacterial genomic DNA (*Current Protocols in Molecular Biology*). Briefly, to the 567 µl of *P. gingivalis* suspension in TE buffer is added 30 µl of 10% SDS and 3 µl of 20 mg/ml proteinase K and the mixture is incubated for one hour at 37° C. To the mixture is added 100 µl of 5M NaCl and 80 µl CTAB/NaCl and incubated for ten minutes at 65° C. The mixture is then extracted with an equal volume of chloroform/isoamyl alcohol, then extracted with phenol/chloroform/isoamyl alcohol, and precipitated in 0.6 volume of isopropanol. The precipitate is washed with 70% ethanol and the DNA pellet is dried, and then resuspended in TE buffer.

DNA may be extracted from a clinical specimen (such as from saliva, tooth scrapings, subgingival material, or gingival tissue) using methods known in the art. For example, cells contained in the specimen may be washed in TE buffer and pelleted by centrifugation. The cells then may be resuspended in 100 µl of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40 TM, 0.045% Tween 20 TM, and 60 µg/ml proteinase K. The sample is incubated at 55° C. water bath for 1 hour. Following the incubation, the sample is incubated at 95° C. for 10 minutes to heat-inactivate the proteinase K. The sample may then be amplified in accordance with the protocol for the polymerase chain reaction as set forth below.

Nucleic Acid Amplification Method:

The purified *P. gingivalis* DNA may be amplified using the polymerase chain reaction (PCR). If purified bacterial DNA is used as a positive control, a concentration of 10–100 pg is usually sufficient for easy detection. DNA to be amplifed is distributed in 0.5 ml microfuge tubes and the volume is adjusted to 30 µl with sterile distilled water. A reaction mixture is prepared in sufficient volume to add 70 µl to each individual reaction tube. Stock reagents for the reaction mixture are mixed in the following proportions for each PCR reaction: 10 µl of 10X PCR buffer (100 mM Tris pH 8.3, 500 mM KCl, 15 mM $MgCl_2$, 0.1% gelatin); 16 µl of dNTPs (1.25 µM each dATP, dCTP, dGTP, dTTP), 2 µM of each positive and negative primer, and 1 unit of Taq polymerase. The total volume is achieved by addition of sterile distilled water. The Taq polymerase is added to the reaction mixture just before use and is gently mixed, not vortexed. The reaction mixture is then added (70 µl/tube) to the tubes containing target DNA to be amplified, and the tubes are gently mixed and briefly centrifuged. A layer of mineral oil, approximately 2 drops, is added to each tube and then the tubes were placed in the thermal cycler. Thirty to thirty-five cycles are generally sufficient for bacterial DNA amplification. One cycle consists of 1 minute at 94° C., 1 minute at 55° C., and 2 minutes at 72° C. The first cycle includes a 5 minute incubation at 94° C. to assure complete denaturation.

Primers for Nucleic Acid Amplification:

Primer sequences which specifically hybridize to *P. gingivalis* genes for the fimbrial protein, superoxide dismutase and collagenase, and used in DNA amplification, are listed in Table 1. The specificity of the primers for *P. gingivalis* was based on a genebank database (Genbank) search for each individual sequence. Each of the primer pairs were used to amplify three strains of *P. gingivalis* designated as 381, A7A1-28, and W50. In each case, primer sequences have been selected arbitrarily for low G-C content and analyzed for self annealing using the Mulfold computer program (Jaeger et al., Oct. 1989, *Proc. Natl. Acad. Sci. U.S.A.* 86:7706–7710). Sequences exhibiting free 3′ and 5′ ends were selected and synthesized on an oligonucleotide synthesizer as phosphoramidites. Primer sequences were purified on Oligonucleotide Purification Cartridges (ABI) according to the manufacturer's directions. Concentrations were determined spectrometrically at 260 nm assuming 1 OD unit is equivalent to 20 µg single stranded oligonucleotide DNA. Optimal conditions for each set of primers for the amplification of *P. gingivalis* DNA was determined by varying the $MgCl_2$ concentration in the PCR buffer, and by adding DMSO or glycerol to the reaction mixture (FIG. 1). Concentrations of $MgCl_2$ ranging from 0.5 mM to 2.5 mM were added to the PCR buffer for amplification of the *P. gingivalis* fimbrial gene. As illustrated in FIG. 1, a concentration of 1.5 mM $MgCl_2$ is sufficient for efficient amplification of the fimbrial gene. Also, the addition of DMSO or glycerol may be beneficial for amplification of the fimbrial gene.

Probes for Amplified Nucleic Acid Detection:

Probe sequences which specifically hybridize to *P. gingivalis* genes for the fimbrial protein, superoxide dismutase and collagenase are listed in Table 1. The specificity of the probe was based on a genebank database (Genbank) search for that sequence. Probe sequences were also selected arbitrarily for low G-C content and analyzed for self annealing using the Mulfold computer program (Jaeger et al., Oct. 1989, *Proc. Natl. Acad. Sci. U.S.A.* 86:7706–7710). Probe sequences were synthesized trytl-off, and were precipitated by butanol as described by Sawadogo and van Dyke (1991, *Nucleic Acid Research* 19(3):674). Concentrations were determined spectrometrically at 260 nm assuming 1 OD unit is equivalent to 20 µg single stranded oligonucleotide DNA.

For detection purposes, the oligonucleotides of the present invention were end-labeled with a radioisotope. Probe sequences, internal to the two primers used for amplification of the gene sequence, were end-labeled using T4 polynucleotide kinase and gamma $^{32}P$ ATP. Twenty pMols of probe DNA in kinase buffer (50 mM Tris, pH 7.6, 10 mM $MgCl_2$, 5 mM dithiothreitol, 0.1 mM spermidine-HCl, 0.1 mM EDTA, pH 8.0) was mixed with 120 µCi of gamma $^{32}P$ ATP and incubated at 37° C. for 1 hour. Labeled probe was separated from unincorporated label on an 8% acrylamide gel run for 1 hour at 200 volts in Tris Borate EDTA (TBE) buffer at room temperature. Labeled probe was first located by exposing the acrylamide gel to x-ray film for three minutes. The resulting autoradiogram was then positioned under the gel, and the band containing the labeled probe was excised from the gel. The gel slice was pulverized in one milliliter of sterile distilled water, and the probe was eluted by shaker incubation overnight at 37° C. The eluted probe was separated from the gel fragments by centrifugation using a chromatography prep column. Radioactivity of the probe was determined, by counting one microliter of the labeled probe on a glass fiber filter, by liquid scintillation.

TABLE 1

P. gingivalis-specific Oligonucleotides

| Oligonucleotide | Sequence | Length | Gene location |
|---|---|---|---|
| Fimbrial gene (Genbank Locus BNGFIMA- 203nt* fragment): | | | |
| Pos. primer: (SEQ ID No: 1) | TTTGGAGTTG GCGATGACGA A | 21 | 269–289 |
| Neg. primer: (SEQ ID No: 2) | GCTTTTACCT CTGCAAGAGT C | 21 | 452–472 |
| Probe: (SEQ ID No: 3) | AAGGTGGCTA AGTTGACCGT AATGGTTTAT AATGGAGAAC A | 41 | 299–338 |
| Superoxide Dismutase gene (Genbank Locus BNGSOD- 493nt fragment): | | | |
| Pos. primer: (SEQ ID No: 4) | ATTTCCCTGC CTTATGCGGT CGATGCACTG GCTCCTGTTA | 40 | 115–154 |
| Neg. Primer: (SEQ ID No: 5) | ACGATTCTGG TAAGTCAGAT AATATGCGTG CTCCCATGC | 39 | 571–606 |
| Probe: (SEQ ID No: 6) | TCATTCGAAA AGTTCAAAGA GGAGTTCAAC ACAGCCGGTA | 40 | 406–445 |
| Collagenase gene (Genbank Locus GNGCLGNS- 381nt fragment): | | | |
| Pos. primer: (SEQ ID No: 7) | ATCTGTCCAC TCAGCTCAAT ATCAGCAATG CGGAAGCCCT A | 41 | 197–237 |
| Neg. Primer: (SEQ ID No: 8) | ATCCATCATC TTATTGATGA AATGAATAGT CTT | 33 | 547–578 |
| Probe: (SEQ ID No: 9) | AAGTGCTATC TAAGCCTGCA CGAACACAA | 29 | 403–431 |

*nt- nucleotide

Detection of Amplified Nucleic Acid Fragments:

Amplified nucleic acid fragments were analyzed on 3% agarose gels in TBE (0.089M Tris, 0.089M boric acid, 2 mM EDTA) containing 0.5 μg/ml ethidium bromide. Fragments were visualized and photographed using UV illumination, and compared to known nucleotide length markers to determine the length of the amplified nucleic acid fragments.

Amplified DNA can be further identified by hybridization with labeled oligonucleotide probes specific to the gene fragment under investigation. Liquid hybridization may be accomplished by mixing end-labeled oligonucleotide probe ($2.5 \times 10^5$ cpm) with amplified DNA (usually approximately 20 μl of the sample from the polymerase chain reaction) in 0.15M NaCl and incubated at 95° C. for 10 minutes to assure complete denaturation of both DNAs; then the mixture was hybridized at 55° C. for one hour. Hybridized DNA was separated from unhybridized probe on a 5% acrylamide gel run in TBE at 200 volts for one hour. The gel was transferred to Whatman filter paper and heat sealed in a bag, and autoradiographed overnight. The amplified DNA fragments can then be visualized on the autoradiographs.

EXAMPLE 2

Detection of Different P. gingivalis Strains

Figure 2:
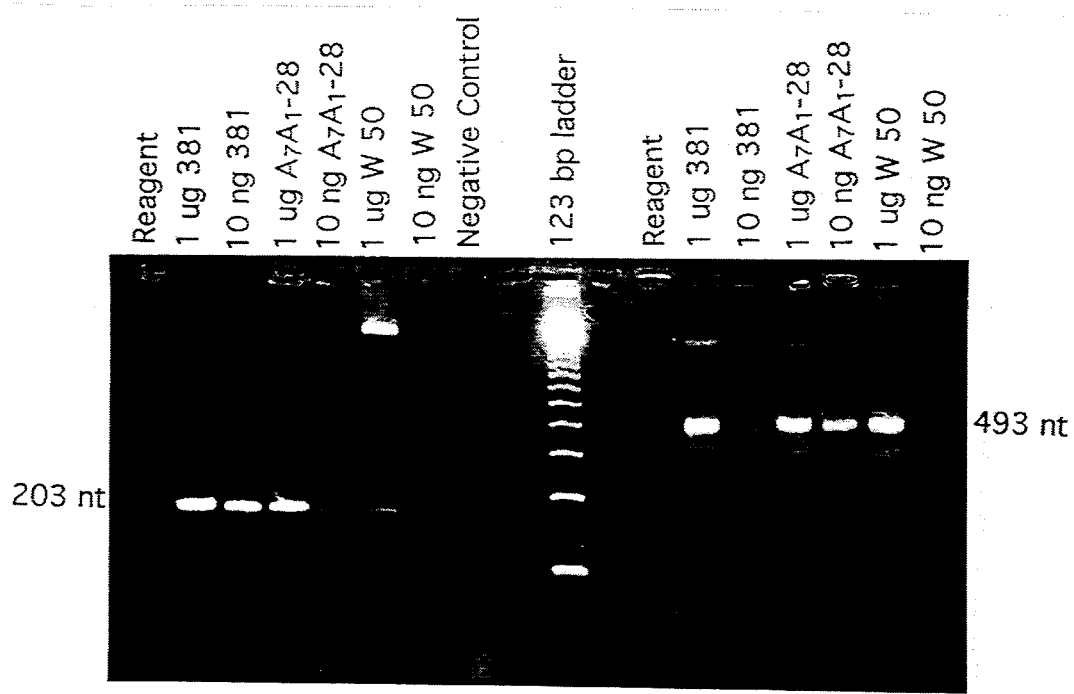
FIG. 2 represents an agarose gel corresponding to the amplification of P. gingivalis DNA at two concentrations, 1 µg and 10 ng, using the fimbrial gene primers or the superoxide dismutase gene primers of the present invention, wherein the DNA is isolated from three strains of P. gingivalis. Lanes 1–8 represent amplification reactions of DNA and controls using the fimbrial gene primers. Lane 9 is the 123 bp ladder reference standard. Lanes 10–16 represent amplification reactions of DNA and controls using the superoxide dismutase gene primers.

This embodiment is in accordance with the procedures and methods described in Example 1. Each of the pairs of primers, illustrated in Table 1, were used to amplify specific sequences of the fimbrial, superoxide dismutase, and collagenase genes from three strains of P. gingivalis (designated as 381, A7A1-28, and W50). The fimbriated P. gingivalis strains 381 and A7A1-28 are of human oral origin, whereas the origin of non-fimbriated strain W50 is unknown, but assumed to be of human origin. Strains 381 and A7A1-28 belong to separate groups based on their immunoreactivity with various anti-fimbriae, and anti-fimbrial peptide antibodies, and on the basis of amino terminal sequence analysis (Lee et al., 1991, Infection and Immunity, 59:383–389). Amplification of the target sequences in 1 μg or 10 ng of genomic DNA from each of the three strains was performed by the polymerase chain reaction. Agarose gel electrophoresis was used to visualize the presence or absence of amplified DNA sequences from the three strains and from the negative controls using the fimbrial gene primers (SEQ ID Nos: 1–2), as shown in the first eight lanes of FIG. 2. The size of the amplified DNA from fimbriated strains 381 and A7A1-28 (FIG. 2, lanes 2–4) is consistent with the expected 203 nt target sequence. The fragment from strain 381 is clearly amplified more strongly than strain A7A1-28 especially at 10 ng of bacterial DNA. Amplified DNA from strain W50 DNA was barely detectable at 1 μg of genomic DNA, and the size appears to be larger than the expected target sequence (FIG. 2, lane 6), suggesting that this non-fimbriated strain may contain a mutated fimbrial gene. FIG. 2 also illustrates the presence or absence of amplified DNA sequences from the three strains and from the negative controls using the primers (SEQ ID Nos: 4–5) for the superoxide dismutase gene sequence (lanes 12–18, located on the right side of the 123 base pair ladder which was used as a reference for size determination). Amplified DNA from the three strains, from 1 μg of bacterial DNA, is clearly visible and is consistent with the expected fragment size of 493 nucleotides. Amplified DNA sequences from 10 ng of bacterial DNA were only weakly visible.

Figure 3:
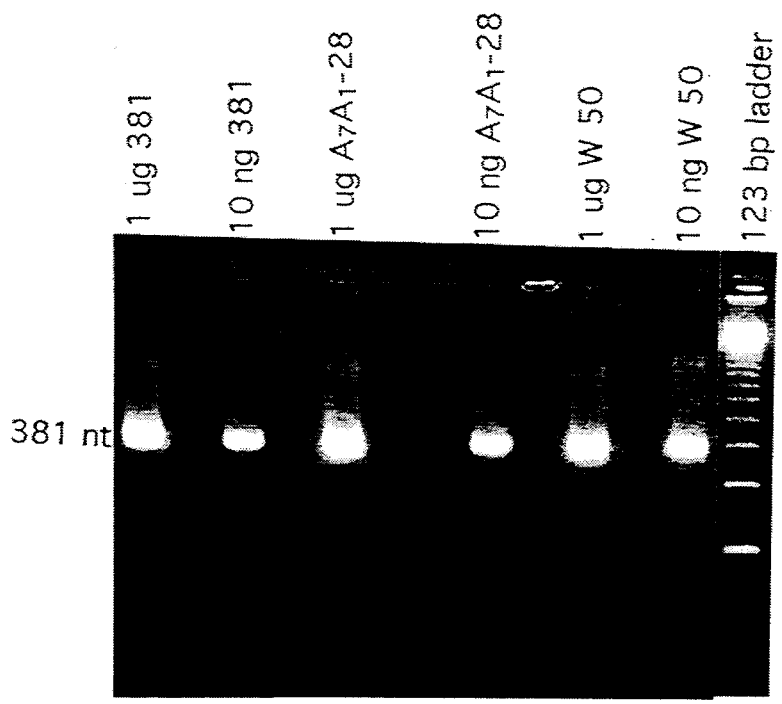
FIG. 3 represents an agarose gel corresponding to the amplification of P. gingivalis DNA at two concentrations, 1 µg and 10 ng, using the collagenase gene primers of the present invention, wherein the DNA is isolated from three strains of P. gingivalis (lanes 1–6). Lane 7 is the 123 bp ladder reference standard.

FIG. 3 illustrates the presence or absence of amplified DNA sequences from the three strains and from the negative controls using the primers specific for the collagenase gene sequence (SEQ ID Nos: 7–8. Amplified DNA from the three strains, from either 10 ng or 1 μg bacterial DNA, is clearly visible and is consistent with the expected fragment size of 381 nucleotides.

EXAMPLE 3

Detection of P. gingivalis DNA in the Presence of Non-Target DNA

Figure 4:
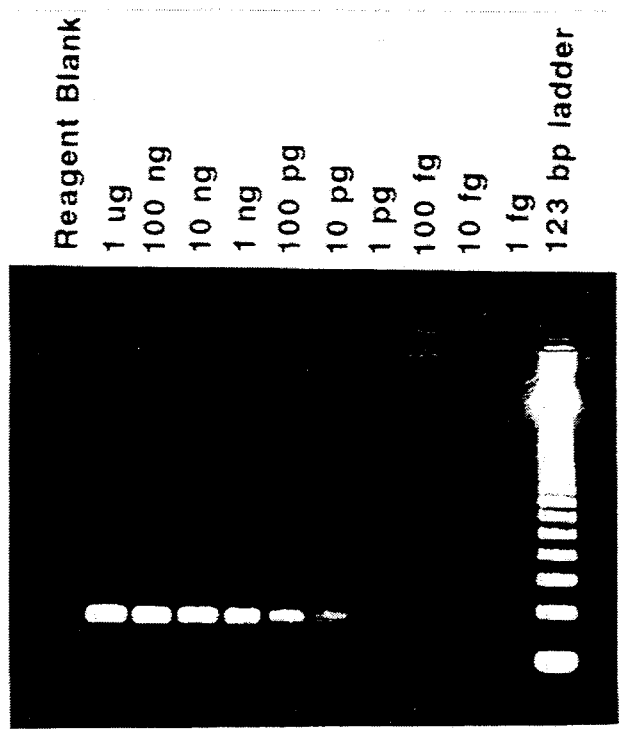
FIG. 4 represents an agarose gel corresponding to P. gingivalis DNA diluted to different concentrations in 10 µg/ml salmon sperm DNA and amplified using the fimbrial gene primers of the present invention.

This embodiment is in accordance with the procedures and methods described in Example 1. To illustrate the specificity and sensitivity of the oligonucleotides and methods of the present invention for the detection of P. gingivalis in clinical samples, P. gingivalis DNA was amplified in the presence of non-target heterologous DNA. DNA isolated from strain 381 was serially diluted in the presence of 10 μg/ml salmon sperm DNA, and the resultant DNA mixture was amplified by polymerase chain reaction using the primers specific for the fimbrial gene sequences. Amplified nucleic acid products were electrophoresed on a 3% agarose gel in the presence of 0.5 μg/ml ethidium bromide, and viewed on a UV transilluminator. As shown in FIG. 4, the only detectable amplified DNA product was of the size consistent with the expected fragment size of the 203 nucleotide target sequence of the P. gingivalis fimbrial gene. Amplified DNA was easily detected from amplification using a concentration of 10 pg of target DNA, and faint bands were visible when only 1–10 fg of target DNA was amplified. It has been estimated that 10 ng of P. gingivalis DNA is equivalent to the DNA of approximately $10^6$ bacterial cells (Groves, in Gene Probes for Bacteria, eds. Macario, and deMacario, Academic Press, 1990, pp. 33–254). Assuming the accuracy of this estimate, and in accordance with the compositions and methods of the present invention, by detecting target DNA sequences amplified from a concentration of 10 fg of bacterial DNA, target sequences are being detected by the amplification of DNA equivalent to that isolated from approximately one bacterial cell.

EXAMPLE 4

Alternative Methods For Detection

Figure 5:
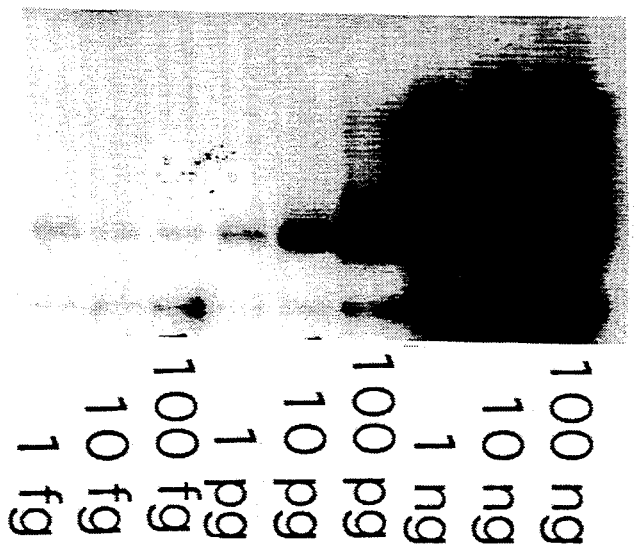
FIG. 5 represents an autoradiogram of liquid hybridized amplified DNA sequences from different dilutions of strain 381 P. gingivalis, amplified using the superoxide dismutase gene primers of the present invention and probed with the superoxide dismutase gene probe of the present invention.
Figure 6:
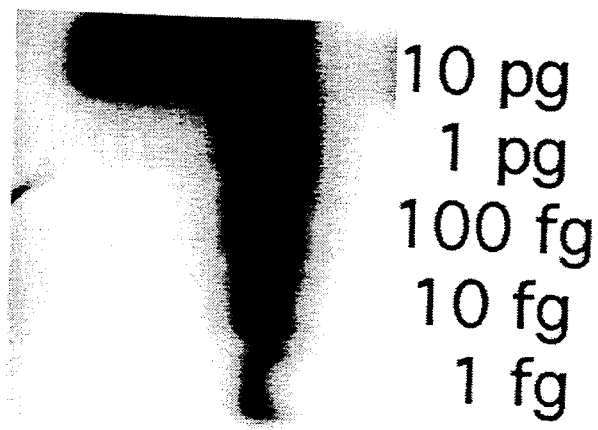
FIG. 6 represents an autoradiogram of liquid hybridized amplified DNA sequences from different dilutions of strain 381 P. gingivalis, amplified using the collagenase gene primers of the present invention and probed with the collagenase gene probe of the present invention.
Figure 1:
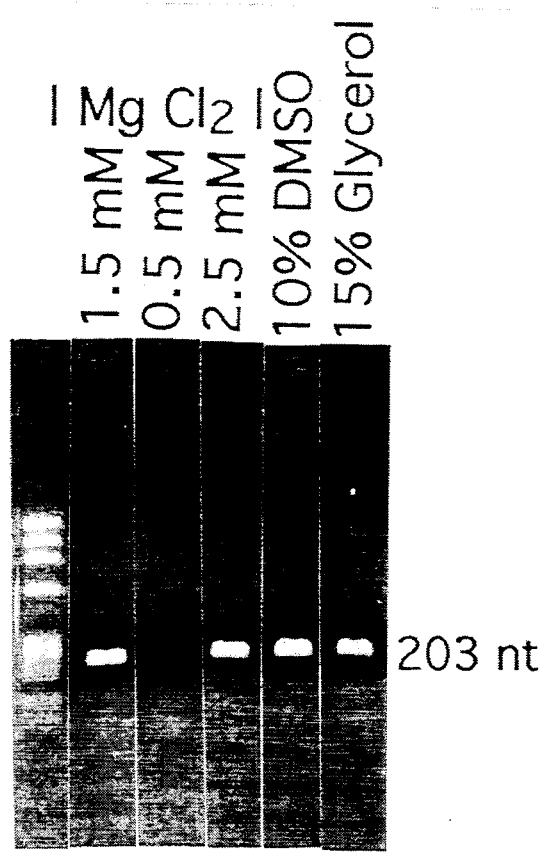
Figure 2:
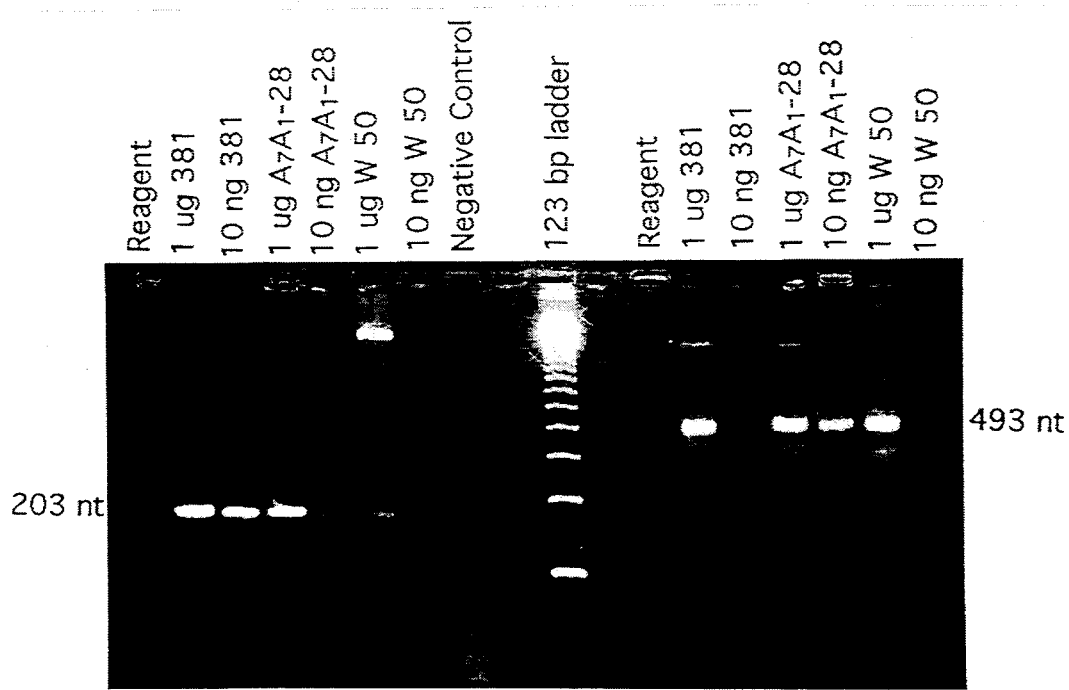
Figure 3:
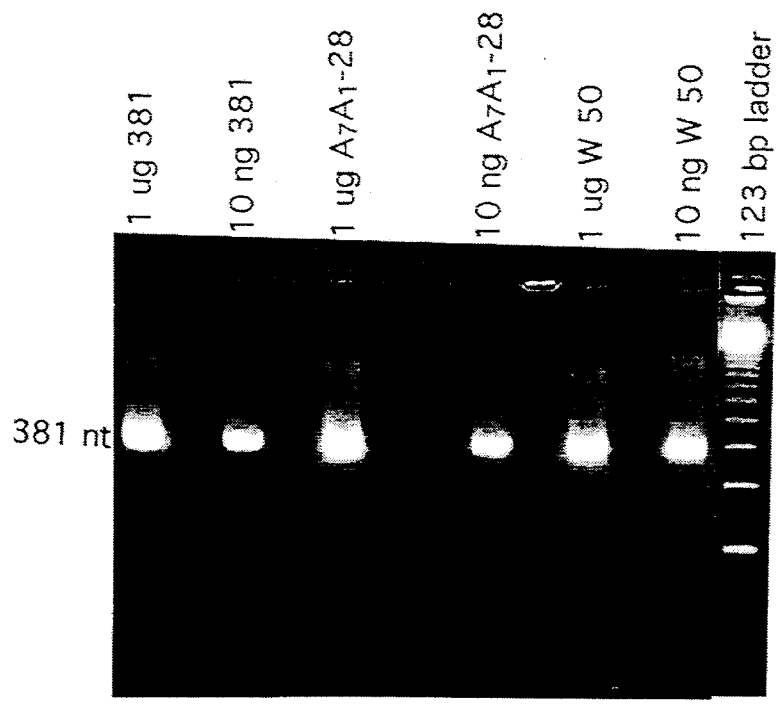
Figure 4:
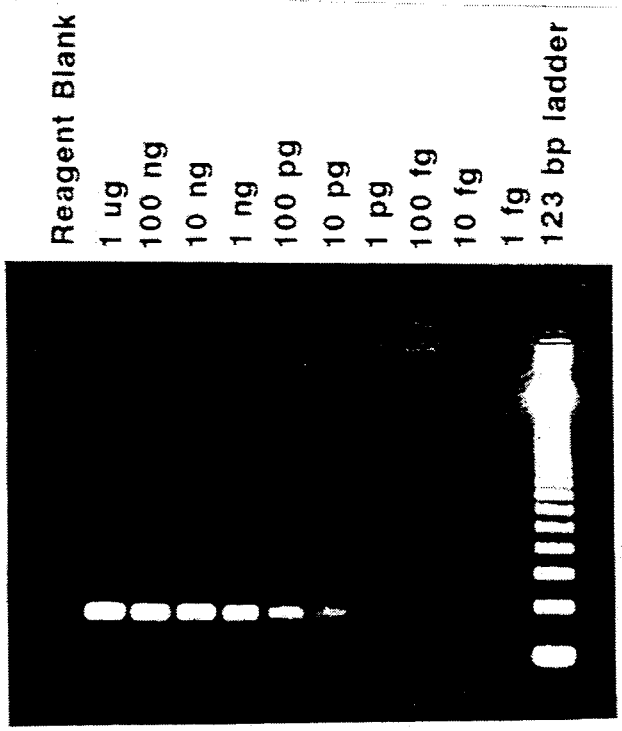
Figure 5:
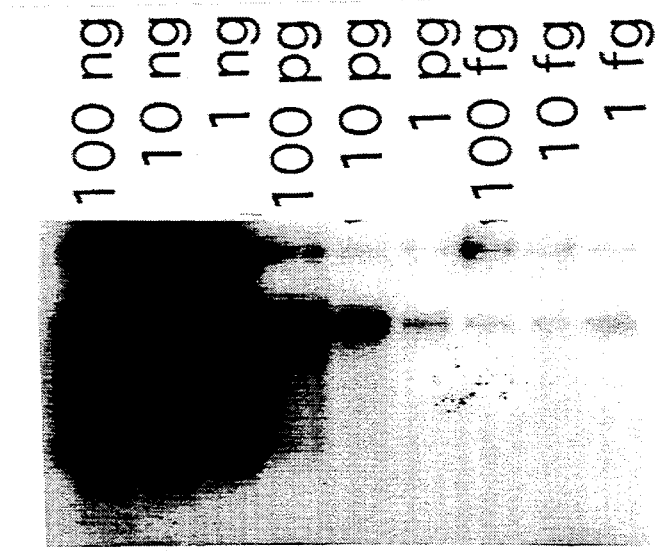
Figure 6:
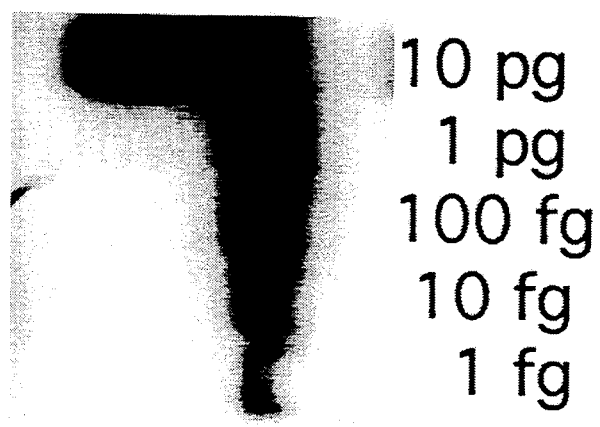

Alternative methods known in the art may be used to improve the detection of amplified target sequences in accordance with the compositions and methods of the present invention. The sensitivity of detection of the amplified DNA sequences can be improved by subjecting the sequences to liquid hybridization. This embodiment is in accordance with the procedures and methods described in Example 1. FIG. 5 illustrates an autoradiogram of liquid hybridized amplified DNA sequences from different dilutions of strain 381 P. gingivalis DNA amplified using primers specific for the superoxide dismutase gene sequences (SEQ ID Nos: 4–5), and detected using labeled probes specific for the superoxide dismutase gene sequences (SEQ ID No: 6). FIG. 6 illustrates the autoradiogram of liquid hybridized amplified DNA sequences from different dilutions of strain 381 P. gingivalis DNA amplified using primers specific for the collagenase gene sequences (SEQ ID Nos: 7–8), and detected using labeled probes specific for the collagenase gene sequences (SEQ ID No: 9). The sensitivity of detection is improved, as the detection from as little as 1–10 fg P. gingivalis DNA is possible using this method of detection.

By scanning the autoradiogram of amplified sequences from known concentrations of P. gingivalis DNA, a linear relationship between band density and concentration of amplified target DNA sequences can be determined. When samples containing an unknown amount of P. gingivalis DNA are amplified and compared to a standard curve of amplified sequences from known concentrations of target DNA, an approximation of the original content of P. gingivalis in the clinical specimen can be obtained. Correspondingly, the number of P. gingivalis bacterial cells may then be approximated.

Alternative methods of detection known in the art, in addition to gel electrophoresis and gel electrophoresis with Southern hybridization and autoradiography, that may be used with the compositions and methods of the present invention include: restriction enzyme digestion with gel electrophoresis; slot-blot hybridization with a labeled oligonucleotide probe; amplification with a radiolabeled primer with gel electrophoresis, Southern hybridization and autoradiography; amplification with a radiolabeled primer with dot blot and autoradiography; amplification with oligonucleotides containing affinity tags (ex. biotin, or one primer incorporating biotin and the other primer with a sequence specific for a DNA binding protein) followed by detection in an affinity-based assay (ex. ELISA); and amplification with oligonucleotides containing fluorophores followed by fluorescence detection.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA from a clinical specimen as in accordance with the procedures and methods described in Example 1. The detection for the presence or absence of amplified target sequences may be accomplished by capturing the amplified target sequences using an affinity matrix having avidin bound thereto, followed by incubation with an avidin conjugate containing an enzyme which can be used to visualize the complex with subsequent substrate development. Alternately, the amplified target sequences may be immobilized by hybridization to the corresponding probes of the target sequence wherein the probes have been affixed onto a matrix. Subsequent detection may be accomplished using an avidin conjugate containing an enzyme which can be used to visualize the complex with subsequent substrate development.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

---

We claim:

1. A composition, for the detection of *Porphyromonas gingivalis*, consisting essentially of a purified and isolated oligonucleotide consisting of a nucleic acid sequence which complements and specifically hybridizes to a conserved region of a *P. gingivalis* gene selected from the group consisting of the fimbrial gene, superoxide dismutase gene, and collagenase gene, wherein said sequence is selected from the group consisting of:

SEQ ID No: 1—TTTGGAGTTG GCGATGACGA A;

SEQ ID No: 2—GCTTTTACCT CTGCAAGAGT C;

SEQ ID No: 3—AAGGTGGCTA AGTTGACCGT AATGGTTTAT AATGGAGAAC A;

SEQ ID No: 4—ATTTCCCTGC CTTATGCGGT CGATGCACTG GCTCCTGTTA;

SEQ ID No: 5—ACGATTCTGG TAAGTCAGAT AATATGCGTG CTCCCATGC;

SEQ ID No: 6—TCATTCGAAAAGTTCAAAGA GGAGTTCAAC ACAGCCGGTA;

SEQ ID No: 7—ATCTGTCCAC TCAGCTCAAT ATCAGCAATG CGGAAGCCCT A;

SEQ ID No: 8—ATCCATCATC TTATTGATGAAATGAATAGT CTT; and

SEQ ID No: 9—AAGTGCTATC TAAGCCTGCA CGAACACAA.

2. A method for detecting the presence or absence of *Porphyromonas gingivalis*, wherein the method comprises the steps of:

(a) lysing the cells in a specimen to release bacterial nucleic acid molecules;

(b) contacting the nucleic acid molecules with oligonucleotides SEQ ID No: 1 and SEQ ID No: 2 of claim 1 under suitable conditions permitting hybridization of the oligonucleotides to the nucleic acid molecules;

(c) enzymatically amplifying a specific region of the nucleic acid molecules comprising target sequences of the *P. gingivalis* fimbrial gene using oligonucleotides SEQ ID No: 1 and SEQ ID No: 2 as primers;

(d) detecting the presence of amplified target sequences of approximately 203 nucleotides in length, wherein the presence of the amplified target sequences correlates to the presence of *P. gingivalis* in the specimen.

3. The method of claim 2, wherein the detection step is performed by labelling at least one of the oligonucleotides with a detectable moiety.

4. The method of claim 2, wherein the detection step is performed by hybridization of the amplified target sequences with oligonucleotide SEQ ID No: 3 as a probe.

5. The method of claim 4, wherein the detection step is performed by labelling the oligonucleotide probe with a detectable moiety.

6. A method for detecting the presence or absence of *Porphyromonas gingivalis*, wherein the method comprises the steps of:

(a) lysing the cells in a specimen to release bacterial nucleic acid molecules;

(b) contacting the nucleic acid molecules with oligonucleotides SEQ ID No: 4 and SEQ ID No: 5 of claim 1 under suitable conditions permitting hybridization of the oligonucleotides to the nucleic acid molecules;

(c) enzymatically amplifying a specific region of the nucleic acid molecules comprising target sequences of the *P. gingivalis* superoxide dismutase gene using oligonucleotides SEQ ID No: 4 and SEQ ID No: 5 as primers;

(d) detecting the presence of amplified target sequences of approximately 493 nucleotides in length, wherein the presence of the amplified target sequences correlates to the presence of *P. gingivalis* in the specimen.

7. The method of claim 6, wherein the detection step is performed by labelling at least one of the oligonucleotides with a detectable moiety.

8. The method of claim 6, wherein the detection step is performed by hybridization of the amplified target sequences with oligonucleotide SEQ ID No: 6 as a probe.

9. The method of claim 8, wherein the detection step is performed by labelling the oligonucleotide probe with a detectable moiety.

10. A method for detecting the presence or absence of *Porphyromonas gingivalis*, wherein the method comprises the steps of:

(a) lysing the cells in a specimen to release bacterial nucleic acid molecules;

(b) contacting the nucleic acid molecules with oligonucleotides SEQ ID No: 7 and SEQ ID No: 8 of claim 1 under suitable conditions permitting hybridization of the oligonucleotides to the nucleic acid molecules;

(c) enzymatically amplifying a specific region of the nucleic acid molecules comprising target sequences of the *P. gingivalis* collagenase gene using oligonucleotides SEQ ID No: 7 and SEQ ID No: 8 as primers;

(d) detecting the presence of amplified target sequences of approximately 381 nucleotides in length, wherein the presence of the amplified target sequences correlates to the presence of *P. gingivalis* in the specimen.

11. The method of claim 10, wherein the detection step is performed by labelling at least one of the oligonucleotides with a detectable moiety.

12. (Amended) The method of claim 10, wherein the detection step is performed by hybridization of the amplified target sequences with oligonucleotide SEQ ID No: 9 as a probe.

13. The method of claim 12, wherein the detection step is performed by labelling the oligonucleotide probe with a detectable moiety.

* * * * *

UNITED STATES PATENT AND TRADEMARK OFFICE
CERTIFICATE OF CORRECTION

PATENT NO. : 5,432,055
DATED : July 11, 1995
INVENTOR(S) : Mary J. Evans; Richard T. Evans; Robert J. Genco; Steven J. Greenberg; and Howard K. Kuramitsu It is certified that error appears in the above-indentified patent and that said Letters Patent is hereby corrected as shown below:

Column 20, claim 12, line 34, delete "(Amended)".

Signed and Sealed this

Thirty-first Day of October 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,432,055
DATED : July 11, 1995
INVENTOR(S) : Mary J. Evans; Richard T. Evans; Robert J. Genco; Steven J. Greenberg; and Howard K. Kuramitsu It is certified that error appears in the above-indentified patent and that said Letters Patent is hereby corrected as shown below:

On the Title page, please add item --[73] Assignee:
The Research Foundation of State University of New York, Buffalo, NY; Health Research Inc., Buffalo, NY; University of Texas Health Science Center, San Antonio, TX.

Page 20, claim 12, line 34, delete "(Amended)".

Signed and Sealed this

First Day of October, 1996

Attest:

BRUCE LEHMAN

Attesting Officer    Commissioner of Patents and Trademarks